(12) United States Patent
Sulikowski et al.

(10) Patent No.: US 11,104,926 B1
(45) Date of Patent: Aug. 31, 2021

(54) PRO-FLUOROPHORE COMPOUNDS AND USE THEREOF

(71) Applicant: Vanderbilt University, Nashville, TN (US)

(72) Inventors: Gary A. Sulikowski, Nashville, TN (US); Kristopher K. Abney, Nashville, TN (US); Susan J. Ramos-Hunter, Nashville, TN (US); Ian M. Romaine, Nashville, TN (US); Charles David Weaver, Nashville, TN (US)

(73) Assignees: Vanderbilt University, Nashville, TN (US); Meharry Medical College, Nashville, TN (US)

( * ) Notice: Subject to any disclaimer, the term of this patent is extended or adjusted under 35 U.S.C. 154(b) by 0 days.

(21) Appl. No.: 16/365,585

(22) Filed: Mar. 26, 2019

Related U.S. Application Data

(60) Provisional application No. 62/648,341, filed on Mar. 26, 2018.

(51) Int. Cl.
*C12P 17/06* (2006.01)
*G01N 33/58* (2006.01)

(52) U.S. Cl.
CPC ............ *C12P 17/06* (2013.01); *G01N 33/582* (2013.01)

(58) Field of Classification Search
None
See application file for complete search history.

(56) References Cited

PUBLICATIONS

Tsien, "A non-disruptive technique for loading calcium buffers and indicators into cells", Nature vol. 290, Apr. 1981, pp. 527-528.
Lavis et al., "Bright Building Blocks for Chemical Biology", ACS Chemical Biology 2014, 9, pp. 855-866.
Zimmerman et al., "Sensitive Assays for Trypsin, Elastase, and Chymotrypsin Using New Fluorogenic Substrates", Analytical Biochemistry 1977, 78, pp. 47-51.
Yokoo et al., "Human mesenchymal stem cells in rodent whole-embryo culture are reprogrammed to contribute to kidney tissues", Proceedings of the National Academy of Sciences of the United States of America 2005, vol. 102, No. 3, pp. 3296-3300.
Forss-Petter et al., "Transgenic Mice Expressing (Beta)-Galactosidase in Mature Neurons Neuron-Specific Enolase Promoter Control", Neuron vol. 5, 1990, pp. 187-197.
Horwitz et al., "Substrates for Cytochemical Demonstration of Enzyme Activitiy" Journal of Medicinal Chemistry 1964, 1, pp. 574-575.
Hofmann et al., "A Kinetic Study on the Enzymatic Hydrolysis of Fluoresceindiacetate and Fluorescein-di-(beta)-D-Galactopyranoside", Analytical Biochemistry 1983, 131, pp. 180-186.
Nolan et al., "Fluorescence-activated cell analysis and sorting of viable mammalian cells based on (Beta)-DGalactosidase activity after transduction of *Escherichia coli* lacZ", Proceedings of the National Academy of Sciences of the United States of America 1988, vol. 85, pp. 2603-2607.
Rakhmanova et al., "A Microplate Fluorimetric Assay for Transfection of the (Beta)-Galactosidase Reporter Gene", Analytical Biochemistry 1998, 257, pp. 234-237.
Lopez Arbeloa et al., "Photophysics of Rhodamines. Molecular Structure and Solvent Effects", The Journal of Physical chemistry 1991, 95, pp. 2203-2208.
Tsien, "The Green Flourescent Protein", Annual Review of Biochemistry 1998, 67, pp. 509-544.
Tian et al., "Selective esterase-ester pair for targeting small molecules with cellular specificity", Proceedings of the National Academy of Sciences 2012, vol. 109, No. 13, pp. 4756-4761.
Junge et al., "Characterization of the Isoenzymes of Pig-Liver Esterase", European Journal of Biochemistry 1979, 95, pp. 519-525.
Lavis et al., "Fluorogenic Label for Biomolecular Imaging", ACS Chemical Biology 2006, vol. 1, No. 4, pp. 252-260.
MacDonald et al., "Evaluation of the Ser-His Dipeptide, a Putative Catalyst of Amide and Ester Hydrolysis", Organic Letters 2016, 18, pp. 3518-3521.
Boo et al., "Synthesis and applications of Rhodamine derivatives as fluorescent probes" Chemical Society Reviews 2009, 38, pp. 2410-2433.
Grimm et al. "Carbofluoresceins and Carborhodamines as Scaffolds for High-Contrast Flourogenic Probes", ACS Chemical Biology 2013, 8, pp. 1303-1310.
Terentyeva et al. "Morpholinecarbonyl-Rhodamine 110 Based Substrates for the Determination of Protease Activity with Accurate Kinetic Parameters" Bioconjugate Chemistry, 22, (2011) pp. 1932-1938.
Sueyoshi et al. "Highly Sensitive and Multiple Enzyme Activity Assay Using Reagent-release Capillary-Isoelectric Focusing with Rhodamine 110-based Substrates" Analytical Sciences, vol. 31, (Nov. 2015) pp. 1155-1161.

*Primary Examiner* — Kagnew H Gebreyesus
(74) *Attorney, Agent, or Firm* — Michael Best & Friedrich LLP

(57) ABSTRACT

Provided are N,N'-diacyl rhodamine compounds, which may be converted to rhodamine by porcine liver esterase (PLE) to produce a fluorescence signal. These compounds may be used, for example, as substrates in enzymatic assays or as labels in cellular imaging.

14 Claims, 7 Drawing Sheets

PRO-FLUOROPHORE COMPOUNDS AND USE THEREOF

CROSS-REFERENCE TO RELATED APPLICATIONS

This application claims the benefit of U.S. Provisional Patent Application No. 62/648,341, filed Mar. 26, 2018, which is incorporated herein by reference in its entirety.

STATEMENT OF GOVERNMENT INTEREST

This invention was made with government support under Grant numbers 2R25-GM059994-18, U54-MD007593, G12-MD007586, U54-CA163069, R24-DA036420, and S10-RR0254970 awarded by the National Institutes of Health (NIH). The government has certain rights in the invention.

TECHNICAL FIELD

The present invention relates to pro-fluorophores compounds, such as N,N'-diacyl rhodamine compounds, method of preparing thereof, and use thereof.

BACKGROUND

For more than 40 years fluorescent molecules like fluorescein and rhodamine have played critical roles in both basic and clinical research. Uses of fluorescent dyes range from fluorescently tagged antibodies useful for determining protein expression and localization, to reporters attached to sensor motifs (e.g. metal ion, reactive oxygen species, pH) to serving as substrates for a broad variety of enzymatic activities.

In the case of enzyme substrates, a common approach is to generate a non-fluorescent pro-dye that acts as a substrate of an enzyme. By the action of the enzyme on the pro-dye substrate a fluorescent product is formed. This approach has been applied using a wide range of enzymes including esterases, peptidases, glycosidases, lactamases, and others.

A commonly used approach for determining where and when proteins are expressed has been use of β-galactosidase combined with a pro-dye substrate. These non-fluorescent pro-dyes are unable to be activated by endogenously expressed enzymes in most animal cells. However, when β-galactosidase is expressed under the control of a cell-type-specific/developmentally specific promoter, the cells expressing the enzyme become competent to activate these dyes. This enables studies of temporal and spatial localization of the promoter of interest as a surrogate for the gene whose expression is normally driven by the promoter. The most commonly used of these pro-dyes is 5-Bromo-4-chloro-3-indolyl-β-D-galactopyranoside, commonly known as X-gal. Unfortunately the product of β-lactamase cleavage of X-gal is a colored but not fluorescent, thus the X-gal/β-galactosidase paired system suffers a lack of sensitivity. In order address the lack of sensitivity of colorimetric products, glycosylated fluorescein pro-dyes have been previously reported, but have yet to find widespread use, possibly due to limitations of loading or applied to fixed cells. In addition, fluoresceins are notably pH-sensitive within the range of physiological pH, further limiting their utility.

In recent years, use of fluorescent proteins such as GFP has to some degree replaced the use of β-galactosidase for localization of expression since years of directed evolution has resulted in the bright, largely pH-insensitive molecules that do not require the addition of exogenous substrates. However, enzyme-based activation of fluorescent dyes offers the advantage of catalysis—many very bright fluorescent molecules can be produced by a single molecule of the activating enzyme. This may lead to dramatic improvements in sensitivity when expression levels of the protein of interest are low. Therefore, even with the advent of GFP-based approaches, there is still a need for enzyme-activated fluorescent dyes.

SUMMARY

The present invention provides a method, which includes reacting a compound of formula (I), or salt thereof, with a porcine liver esterase (PLE),

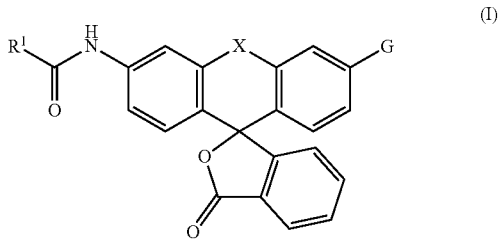

wherein
X is O, $CR^xR^y$, or $SiR^xR^y$;
G is —OH, —$NH_2$, —$OC(O)R^2$, or —$NHC(O)R^2$;
$R^x$ and $R^y$ are each independently H or $C_{1-4}$alkyl;
$R^1$ and $R^2$ are independently $C_{1-6}$alkyl, $C_{1-6}$haloalkyl, $C_{3-8}$cycloalkyl, 6- to 10-membered aryl, 5- to 8-membered heteroaryl, or 5- to 8-membered heterocycle, wherein the cycloalkyl, aryl, heteroaryl, and heterocycle are optionally substituted, wherein the heteroaryl and heterocycle are attached to the —C(O)— group through a carbon atom;
whereby a fluorescence signal is produced.

In some embodiments, the compound is a compound of formula (I-a), or a salt thereof,

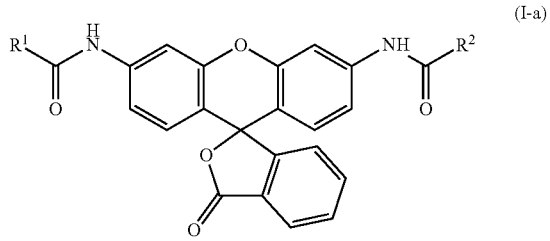

wherein $R^1$ and $R^2$ are as defined in formula (I).

In some embodiments, the method may be used to conduct an enzymatic assay. For example, the fluorescence signal produced from the reaction may be measured to determine the amount and/or activity of the porcine liver esterase.

In some embodiments, the method may be used to image a biological sample, such as a cell or a tissue. For example, a compound of formula (I) may enter a cell and react with the porcine liver esterase expressed by the cell, thereby producing fluorescence which may be visualized to produce an image of the cell.

BRIEF DESCRIPTION OF THE DRAWINGS

FIG. 2A shows absorption and emission spectra of 1c in the presence and absence of PLE. The inset shows a cuvette containing 1c in the presence or absence of PLE illuminated with a violet laser. Inserted images in FIG. 2A were acquired with an iPhone6 (Apple) while samples in cuvettes were illuminated with a hand-held, violet laser pointer. FIG. 2B shows comparison of various amidated rhodamines (10 µM) for 2 min at 22° C. in the presence of 30 nM PLE (excitation 480±20 nm, emission 540±20 nm). Y axis are normalized to the maximum observed fluorescence under the experimental conditions. Error bars represent the standard error of the mean (SEM) of 4 independent replicates.

FIG. 3A shows time-dependent increase in fluorescence in wild-type and PLE-expressing HEK293 cells upon addition of 3 µM 1c (excitation 480±20 nm, emission 540±20 nm). The Y axis is normalized to the maximum observed fluorescence under the experimental conditions. FIG. 3B shows fluorescence observed after treatment of wild-type or PLE-expressing HEK293 for 2 min at 22° C. with 10 µM 1a-1f as well as 300 nM fluorescein diacetate (FDA), a substrate for esterases expressed in both wild-type and PLE-expressing HEK293 cells. All data are representative of 4 independent replicates.

DETAILED DESCRIPTION

Figure 1:
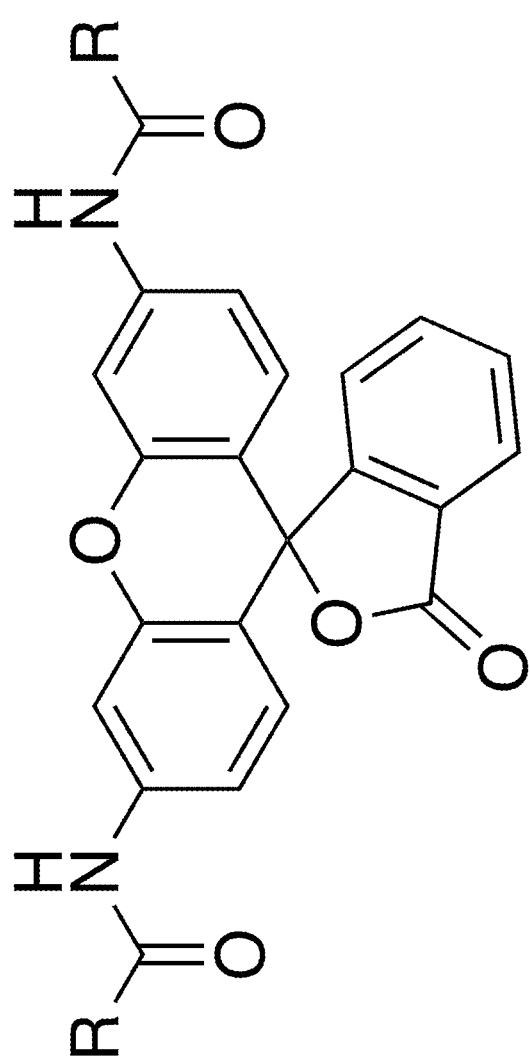
FIG. 1 shows representative N,N'-diacyl rhodamine compounds disclosed herein.

The present disclosure relates to synthesis and testing of a family of rhodamine pro-fluorophores and an enzyme capable of converting pro-fluorophores to a fluorescent product, such as Rhodamine 110. A library of simple N,N'-diacyl rhodamines was prepared and the ability of porcine liver esterase (PLE) as an enzyme to activate rhodamine-based pro-fluorophores was investigated. A PLE-expressing cell line generated an increase in fluorescence rapidly upon pro-fluorophore addition, which demonstrates that the rhodamine pro-fluorophores disclosed herein may be readily taken up by the cell and produce fluorescence upon PLE-mediated release. In particular, rhodamine pro-fluorophore amides trifluoroacetamide (TFAm) and proponamide (PAm) may be used as substrates in a cell-based assay using PLE expressing HEK293. The pro-fluorophore compounds disclosed herein may diffuse into live cells and resist endogenous hydrolysis. The use of an engineered cell line containing the exogenous enzyme PLE may demonstrate the rigorousness of amide masking when compared to cells not containing PLE. The pro-flurophore rhodamine compounds disclosed herein paired with PLE may be used in vitro and in vivo fluorescence based assays.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The compounds as described herein contain the variables that encompass specific groups (e.g., alkyl and cycloalkyl). As one of ordinary skill in the art will recognize, combinations of substituents envisioned by this disclosure are those combinations that result in the formation of stable or chemically feasible compounds. The term "stable," as used herein, refers to compounds that are not substantially altered when subjected to conditions to allow for their production, detection, and preferably their recovery or purification. In some embodiments, a stable compound or chemically feasible compound is one that is not substantially altered when kept at a temperature of 40° C. or less, in the absence of moisture or other chemically reactive conditions, for at least a week.

The terms "comprise(s)," "include(s)," "having," "has," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

Definitions of specific functional groups and chemical terms are described in more detail below. For purposes of this disclosure, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 3$^{rd}$ Edition, Cambridge University Press, Cambridge, 1987; the entire contents of each of which are incorporated herein by reference.

The term "alkyl" as used herein, means a straight or branched chain saturated hydrocarbon. Representative examples of alkyl include, but are not limited to, methyl, ethyl, npropyl, isopropyl, n-butyl, sec-butyl, isobutyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylene," as used herein, means a divalent group derived from a straight or branched chain saturated hydrocarbon. Representative examples of alkylene include, but are not limited to, —CH$_2$—, —CH$_2$CH$_2$—, —CH$_2$CH$_2$CH$_2$—, —CH$_2$CH(CH$_3$)CH$_2$—, and CH$_2$CH (CH$_3$)CH(CH$_3$)CH$_2$—.

The term "aryl" as used herein, means phenyl or a bicyclic aryl. Representative examples of the bicyclic aryl include, but are not limited to, naphthyl, dihydronaphthalenyl, tetrahydronaphthalenyl, indanyl, and indenyl. The phenyl and bicyclic aryls are attached to the parent molecular moiety through any carbon atom contained within the phenyl or bicyclic aryl.

The term "cycloalkyl" as used herein, means a monovalent group derived from an all-carbon ring system containing zero heteroatoms as ring atoms, and zero double bonds. The all-carbon ring system can be a monocyclic, bicyclic, or tricyclic ring system, and can be a fused ring system, a bridged ring system, or a spiro ring system, or combinations thereof. Examples of cycloalkyls include, but are not limited to, cyclopropyl, cyclobutyl, cyclopentyl, cyclohexyl, cycloheptyl, and cyclooctyl. The cycloalkyl groups described herein can be appended to the parent molecular moiety through any substitutable carbon atom.

The term "halogen" means a chlorine, bromine, iodine, or fluorine atom.

The term "haloalkyl," as used herein, means an alkyl, as defined herein, in which one, two, three, four, five, six, or seven hydrogen atoms are replaced by halogen. Representative examples of haloalkyl include, but are not limited to, 2-fluoroethyl, difluoromethyl, trifluoromethyl, 2,2,2-trifluoroethyl, 2,2,2-trifluoro-1, 1-dimethylethyl, and the like.

The term "heteroaryl," as used herein, refers to a monocyclic heteroaryl or a bicyclic heteroaryl. The monocyclic heteroaryl is a five- or six-membered ring. The five-membered ring contains two double bonds. The five-membered ring may contain one heteroatom selected from O or S; or one, two, three, or four nitrogen atoms and optionally one oxygen or sulfur atom. The six-membered ring contains three double bonds and one, two, three or four nitrogen atoms. Representative examples of monocyclic heteroaryl include, but are not limited to, furanyl, imidazolyl, isoxazolyl, isothiazolyl, oxadiazolyl, 1,3-oxazolyl, pyridinyl, pyridazinyl, pyrimidinyl, pyrazinyl, pyrazolyl, pyrrolyl, tetrazolyl, thiadiazolyl, 1,3-thiazolyl, thienyl, triazolyl, and triazinyl. The bicyclic heteroaryl includes a monocyclic heteroaryl fused to a phenyl, or a monocyclic heteroaryl fused to a monocyclic cycloalkyl, or a monocyclic heteroaryl fused to a monocyclic cycloalkenyl, or a monocyclic heteroaryl fused to a monocyclic heteroaryl, or a monocyclic heteroaryl fused to a monocyclic heterocycle. Representative examples of bicyclic heteroaryl groups include, but are not limited to, benzofuranyl, benzothienyl, benzoxazolyl, benzimidazolyl, benzoxadiazolyl, 6,7-dihydro-1,3-benzothiazolyl, imidazo[1,2-a]pyridinyl, indazolyl, indolyl, isoindolyl, isoquinolinyl, naphthyridinyl, pyridoimidazolyl, quinazolinyl, quinolinyl, thiazolo[5,4-b]pyridin-2-yl, thiazolo[5,4-d]pyrimidin-2-yl, 5,6,7,8-tetrahydroquinolin-5-yl, cyclopenta[b]thiophen-2-yl, and 4,5,6,7-tetrahydrobenzo[b]thiophen-2-yl. The heteroaryl groups may be connected to the parent molecular moiety through any substitutable carbon atom or any substitutable nitrogen atom contained within the group. In some embodiments, the heteroaryl group is connected to the parent molecular moiety through a carbon atom.

The terms "heterocycle" or "heterocyclic" refer generally to ring systems containing at least one heteroatom as a ring atom where the heteroatom is selected from oxygen, nitrogen, and sulfur. In some embodiments, a nitrogen or sulfur atom of the heterocycle is optionally substituted with oxo. Heterocycles may be a monocyclic, bicyclic, or tricyclic ring system, and can be a fused ring system, a bridged ring system, or a spiro ring system, or combinations thereof. The monocyclic heterocycle is generally a 4, 5, 6, 7, or 8-membered non-aromatic ring containing at least one heteroatom selected from O, N, or S. The 4-membered ring contains one heteroatom and optionally one double bond. The 5-membered ring contains zero or one double bond and one, two or three heteroatoms. The 6, 7, or 8-membered ring contains zero, one, or two double bonds, and one, two, or three heteroatoms. Representative examples of monocyclic heterocycle include, but are not limited to, azetidinyl, azepanyl, diazepanyl, 1,3-dioxanyl, 1,4-dioxanyl, 1,3-dioxolanyl, 4,5-dihydroisoxazol-5-yl, 3,4-dihydropyranyl, 1,3-dithiolanyl, 1,3-dithianyl, imidazolinyl, imidazolidinyl, isothiazolinyl, isothiazolidinyl, isoxazolinyl, isoxazolidinyl, morpholinyl, oxadiazolinyl, oxadiazolidinyl, oxazolinyl, oxazolidinyl, oxetanyl, piperazinyl, piperidinyl, pyranyl, pyrazolinyl, pyrazolidinyl, pyrrolinyl, pyrrolidinyl, tetrahydrofuranyl, tetrahydropyranyl, tetrahydrothienyl, thiadiazolinyl, thiadiazolidinyl, thiazolinyl, thiazolidinyl, thiomorpholinyl, 1,1-dioxidothiomorpholinyl, thiopyranyl, and trithianyl. The fused bicyclic heterocycle is a 7-12-membered ring system having a monocyclic heterocycle fused to a phenyl, to a saturated or partially saturated carbocyclic ring, or to another monocyclic heterocyclic ring, or to a monocyclic heteroaryl ring. Representative examples of fused bicyclic heterocycle include, but are not limited to, 1,3-benzodioxol-4-yl, 1,3-benzodithiolyl, 3-azabicyclo[3.1.0]hexanyl, hexahydro-1H-furo[3,4-c]pyrrolyl, 2,3-dihydro-1,4-benzodioxinyl, 2,3-dihydro-1-benzofuranyl, 2,3-dihydro-1-benzothienyl, 2,3-dihydro-1H-indolyl, 5,6,7,8-tetrahydroimidazo[1,2-a]pyrazinyl, and 1,2,3,4-tetrahydroquinolinyl. Spiro heterocycle means a 4-, 5-, 6-, 7-, or 8-membered monocyclic heterocycle ring wherein two of the substituents on the same carbon atom form a second ring having 3, 4, 5, 6, 7, or 8 members. Examples of a spiro heterocycle include, but are not limited to, 1,4-dioxa-8-azaspiro[4.5]decanyl, 2-oxa-7-azaspiro[3.5]nonanyl, 2-oxa-6-azaspiro[3.3]heptanyl, and 8-azaspiro[4.5]decane. The heterocycle groups of the present disclosure may contain an alkylene bridge of 1, 2, or 3 carbon atoms, linking two nonadjacent atoms of the group. Examples of such a bridged heterocycle include, but are not limited to, 2,5-diazabicyclo[2.2.1]heptanyl, 2-azabicyclo[2.2.1]heptanyl, 2-azabicyclo[2.2.2]octanyl, and oxabicyclo[2.2.1]heptanyl. The heterocycle groups may be connected to the parent molecular moiety through any substitutable carbon atom or any substitutable nitrogen atom contained within the group. In some embodiments, the heterocycle group is connected to the parent molecular moiety through a carbon atom.

The term "oxo" as used herein refers to an oxygen atom bonded to the parent molecular moiety. An oxo may be attached to a carbon atom or a sulfur atom by a double bond. Alternatively, an oxo may be attached to a nitrogen atom by a single bond, i.e., an N-oxide.

Terms such as "alkyl," "cycloalkyl," "alkylene," etc. may be preceded by a designation indicating the number of atoms present in the group in a particular instance (e.g., "$C_{1-4}$alkyl," "$C_{3-6}$cycloalkyl," "$C_{1-4}$alkylene"). These designations are used as generally understood by those skilled in the art. For example, the representation "C" followed by a subscripted number indicates the number of carbon atoms present in the group that follows. Thus, "$C_3$alkyl" is an alkyl group with three carbon atoms (i.e., n-propyl, isopropyl). Where a range is given, as in "$C_{1-4}$," the members of the group that follows may have any number of carbon atoms falling within the recited range. A "$C_{1-4}$alkyl," for example, is an alkyl group having from 1 to 4 carbon atoms, however arranged (i.e., straight chain or branched).

When a substituent or group is referred to as "unsubstituted" or not referred to as "substituted" or "optionally substituted," it means that the substituent or group does not have any substituents. If a substituent or group is described as being "optionally substituted," the substituent or group may be either (1) unsubstituted or (2) substituted. If a substituent or group is described as being optionally substituted with up to a particular number of non-hydrogen radicals, the substituent or group may be either (1) unsubstituted; or (2) substituted by up to that particular number of non-hydrogen radicals or by up to the maximum number of substitutable positions on the substituent, whichever is less. Thus, for example, if a substituent is described as a heteroaryl optionally substituted with up to 3 non-hydrogen radicals, then any heteroaryl with less than 3 substitutable positions would be optionally substituted by up to only as many non-hydrogen radicals as the heteroaryl has substitutable positions. To illustrate, tetrazolyl (which has only one substitutable position) would be optionally substituted with up to one non-hydrogen radical. To illustrate further, if an amino nitrogen is described as being optionally substituted with up to 2 non-hydrogen radicals, then a primary amino nitrogen will be optionally substituted with up to 2 non-hydrogen radicals, whereas a secondary amino nitrogen will be optionally substituted with up to only 1 non-hydrogen radical.

As used herein, the term "substituent" or "suitable substituent" is intended to mean a chemically acceptable functional group e.g., a moiety that does not negate the activity of the inventive compounds. Illustrative examples of suitable substituents include, but are not limited to halo groups, perfluoroalkyl groups, perfluoroalkoxy groups, alkyl groups, alkenyl groups, alkynyl groups, hydroxy groups, halo groups, oxo groups, mercapto groups, alkylthio groups, alkoxy groups, nitro groups, azidealkyl groups, sulfonic acid groups, aryl or heteroaryl groups, aryloxy or heteroaryloxy groups, aralkyl or heteroaralkyl groups, aralkoxy or heteroaralkoxy groups, HO—(C=O)— groups, heterocyclic groups, cycloalkyl groups, amino groups, alkyl- and dialkylamino groups, carbamoyl groups, alkylcarbonyl groups, alkylcarbonyloxy groups, alkoxycarbonyl groups, alkylaminocarbonyl groups, dialkylamino carbonyl groups, arylcarbonyl groups, aryloxycarbonyl groups, alkylsulfonyl groups, arylsulfonyl groups and the like. The substituents may be substituted by additional substituents. The substituents may also be in salt forms (e.g., a sulfonic acid group can be in the form of a sulfonate group).

If substituents are described as being "independently selected" from a group, each substituent is selected independent of the other. Each substituent, therefore, may be identical to or different from the other substituent(s).

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I. The structures also include zwitterioinc forms of the compounds or salts of formula I where appropriate.

2. Method

In one aspect, the present disclosure provides a method, which comprises reacting a compound of formula (I), or salt thereof, with a porcine liver esterase (PLE),

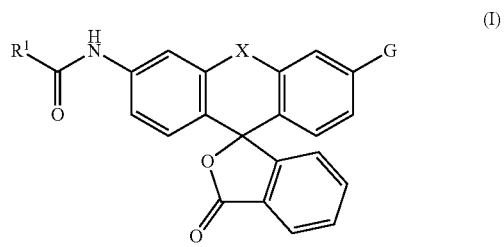

wherein
X is O, $CR^xR^y$, or $SiR^xR^y$;
G is —OH, —$NH_2$, —$OC(O)R^2$, or —$NHC(O)R^2$;
$R^x$ and $R^y$ are each independently H or $C_{1-4}$alkyl;
$R^1$ and $R^2$ are independently $C_{1-6}$alkyl, $C_{1-6}$haloalkyl, $C_{3-8}$cycloalkyl, 6- to 10-membered aryl, 5- to 8-membered heteroaryl, or 5- to 8-membered heterocycle, wherein the cycloalkyl, aryl, heteroaryl, and heterocycle are optionally substituted, wherein the heteroaryl and heterocycle are attached to the —C(O)— group through a carbon atom;
whereby a fluorescence signal is produced.

2.1 PLE Enzyme

Although PLE enzymes are known to have esterase activity, it is surprisingly observed herein that PLE may also exhibit amidase activity. In particular, the porcine liver esterase as used herein may be capable of catalyzing the hydrolysis of the compounds of formula (I). In some embodiments, the porcine liver esterase catalyzes the hydrolysis of the amide bond (—C(O)—NH—) of the compounds disclosed herein, resulting in the production of Rhodamine 110, or a salt thereof, which is fluorescent. Advantageously, the fluorescence of rhodamine (such as Rhodamine 110) is considerably less pH sensitive than other readily available fluorescent molecules (such as fluorescein) in the physiological range.

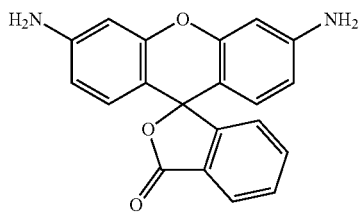

Rhodamine 110

Suitable PLE enzymes may include commercial, isolated, or recombinant porcine liver esterase proteins. In some embodiments, the PLE enzyme is a porcine liver esterase protein expressed in a cell. For example, the PLE enzyme may be expressed in HEK293 cells.

2.2 Substrate Compound

In some embodiments, the compound is a compound of formula (I), or a salt thereof, wherein X is O. In some embodiments, the compound is a compound of formula (I), or a salt thereof, wherein G is —NHC(O)R². In some embodiments, the compound is a compound of formula (I-a), or a salt thereof,

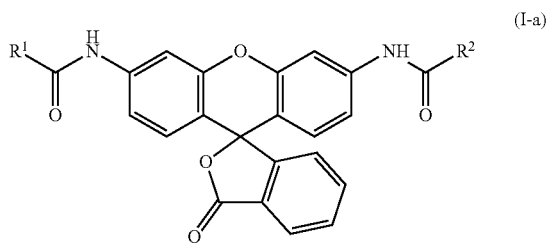

(I-a)

wherein R¹ and R² are as defined in formula (I).

The compounds of formula (I) or formula (I-a), or salts thereof, may be used as substrates of the porcine liver esterase. In some embodiments, R¹ and R² are independently $C_{1-6}$alkyl, $C_{1-6}$haloalkyl, or phenyl. In some embodiments, R¹ and R² are independently $C_{1-4}$alkyl or $CF_3$. In some embodiments, R¹ and R² are both $C_{1-4}$alkyl (such as —$CH_2CH_3$ or i-$C_3H_7$) or —$CF_3$. In some embodiments, R¹ and R² are both —$CF_3$. In some embodiments, R¹ and R² are both —$CH_3$, —$CH_2CH_3$, tert-$C_4H_9$, or phenyl. In some embodiments, R¹ and R² are both —$CH_2CH_3$. Examples of suitable compounds include, but are not limited to, those shown in FIG. 1, or salts thereof.

Advantageously, the compounds disclosed herein may be non-fluorescent in its free or salt form, thus reducing the background signal when used in the present methods. Further, the compounds disclosed herein may be rapidly hydrolyzed by PLE, but are not hydrolyzed to any detectable degree by other enzymes (such as the endogenous esterase enzymes in a cell). In embodiments, the compounds or salts thereof are not fluorescent, and are selectively hydrolyzed by PLE to produce a fluorescent signal in an in vitro or in vivo method.

The compounds disclosed herein may be prepared, for example, by acylation of rhodamine or rhodol. In some embodiments, commercial Rhodamine 110 may be acylated using either acyl anhydride or acyl chloride under suitable reaction conditions to provide the N,N'-diacyl rhodamine products in high yield (about 40-90%).

The compounds described herein may be in the form of a salt. The compound may differ from the corresponding salts in certain physical properties, such as solubility in polar solvents, but otherwise the salts are equivalent to the compound for the purposes of this disclosure.

For example, if the compound is anionic, or has a functional group which may be anionic (e.g., —COOH may be —COO), then a salt may be formed with a suitable cation. Examples of suitable inorganic cations include, but are not limited to, alkali metal ions such as $Na^+$ and $K^+$, alkaline earth cations such as $Ca^{2+}$ and $Mg^{2+}$, and other cations. Examples of suitable organic cations include, but are not limited to, ammonium ion (i.e., $NH_4^+$) and substituted ammonium ions, such as those derived from ethylamine, diethylamine, dicyclohexylamine, triethylamine, butylamine, ethylenediamine, ethanolamine, diethanolamine, piperazine, benzylamine, phenylbenzylamine, choline, meglumine, and tromethamine, as well as amino acids, such as lysine and arginine.

If the compound is cationic, or has a functional group that may be cationic (e.g., —$NH_2$ may be —$NH_3$), then a salt may be formed with a suitable anion. Examples of suitable inorganic anions include, but are not limited to, those derived from hydrochloric, hydrobromic, hydroiodic, sulfuric, sulfurous, nitric, nitrous, or phosphoric acid. Examples of suitable organic anions include, but are not limited to, those derived from 2-acetyoxybenzoic, acetic, ascorbic, aspartic, benzoic, camphorsulfonic, cinnamic, citric, edetic, ethanedisulfonic, ethanesulfonic, fumaric, glucoheptonic, gluconic, glutamic, glycolic, hydroxymaleic, hydroxynaphthalene carboxylic, isethionic, lactic, lactobionic, lauric, maleic, malic, methanesulfonic, mucic, oleic, oxalic, palmitic, pamoic, pantothenic, phenylacetic, phenylsulfonic, propionic, pyruvic, salicylic, stearic, succinic, sulfanilic, tartaric, toluenesulfonic, or valeric acid.

2.3 Sample

The present methods may be used to assay or image a sample. The sample may contain biological components. The sample may include a cell and/or one or more cell components. The sample may include one or more components selected from intact cells, cell extracts, cell lysates, bacteria, viruses, organelles, exosomes, natural or synthetic amino acid, nucleic acid, carbohydrates, lipids, and membrane complexes. The sample may be a heterogeneous or homogenous mixture of the foregoing components.

The sample may include an animal (e.g., a vertebrate), a plant, a fungus, physiological fluid (e.g., blood, plasma, urine, mucous secretions and the like), a cell, a cell lysate, a cell supernatant, or a purified fraction of a cell (e.g., a subcellular fraction). In certain embodiments, the sample may be a cell. In some embodiments, the sample may be a live cell. The cell may be a eukaryotic cell, e.g., yeast, avian, plant, insect or mammalian cells, including but not limited to human, simian, murine, canine, bovine, equine, feline, ovine, caprine or swine cells, or prokaryotic cells, or cells from two or more different organisms, or cell lysates or supernatants thereof. The cells may not have been genetically modified via recombinant techniques (nonrecombinant cells), or may be recombinant cells which are transiently transfected with recombinant DNA and/or the genome of which is stably augmented with a recombinant DNA, or which genome has been modified to disrupt a gene, e.g., disrupt a promoter, intron or open reading frame, or replace one DNA fragment with another. The recombinant DNA or replacement DNA fragment may encode a molecule to be detected by the methods of the present disclosure, a moiety which alters the level or activity of the molecule to be detected, and/or a gene product unrelated to the molecule or moiety that alters the level or activity of the molecule. The cells may be otherwise genetically modified via recombinant techniques.

The sample may include a porcine liver esterase capable of hydrolyzing the compounds disclosed herein or salts thereof. In some embodiments, the sample is a biological sample obtained from a cell or an animal. For example, the sample may be a cell lysate, extracellular vesicles, a live cell, a tissue (such as fixed tissue), or combinations thereof. In some embodiments, the sample is a live cell expressing PLE. In particular embodiments, the sample is a HEK293 cell expressing PLE.

2.4 Method of Use

In some embodiments, the method is a method of assaying a sample comprising a porcine liver esterase. For example, the method may include contacting the sample with a compound of formula (I) or formula (I-a), or salt thereof, whereby the PLE in the sample reacts with the compound, or salt thereof, and a fluorescence signal is produced. The method may further include measuring the fluorescence signal. The fluorescence signal may be measured by any suitable fluorescence spectrometers known in the art.

In some embodiments, the method is a method of imaging a sample comprising a porcine liver esterase. For example, the method may include contacting the sample with a compound of formula (I) or formula (I-a), or salt thereof, whereby the PLE in the sample reacts with the compound, or salt thereof, and a fluorescence signal is produced. The method may further include imaging the sample, for example, by visualizing and/or recording the fluorescence signal from the sample. The imaging process may be carried out using any suitable fluorescence microscopy techniques known in the art. In some embodiments, the imaging is carried out using a confocal microscope.

In some embodiments, the sample contains a cell, such as a live cell expressing the PLE. The cell may be allowed to contact with a compound of formula (I) or formula (I-a), or salt thereof. The contacting may be carried out, for example, by incubating the cell and the compound, or salt thereof, in a medium, such as a liquid medium. The incubation may be performed under conditions that do not interfere with the physiological functions of the cell. For example, the cell may be a live cell and the compound or salt thereof may be incubated with the cell in a cell culture medium.

In some embodiments, the sample contains a cell over-expressing a PLE protein. The overexpression may be performed, for example, using known recombinant technology and suitable vectors. In some embodiments, the cell is a HEK293 cell transfected with a vector to express PLE. In some embodiments, the expression (e.g., overexpression) of PLE does not cause discernable difference in growth rate or morphology of the cell.

In particular embodiments, the sample contains a cell expressing PLE in the cytoplasm. Upon contacting the cell, a compound disclosed herein, or a salt thereof, may enter the cell, such that the PLE in the cytoplasm may react with the compound, or salt thereof, to produce a fluorescence signal. Subsequently, the cell may be imaged based on the fluorescence signal. Alternatively, the PLE activity may be assayed by measuring the fluorescence signal produced in the cell.

Advantageously, the present disclosure provides pro-fluorophores such as N,N'-diacyl rhodamine compounds, which may be readily taken up by a cell and activated by PLE to produce bright, pH-insensitive fluorescence. In particular, the present disclosure provides a direct, amidase mechanism to activate pro-fluorophores by PLE. Thus, the present disclosure may extend the use of PLE to an activating enzyme for amide derivatives of Rhodamine 110. Further, the unique ability of PLE to hydrolyze the present compounds to release a fluorescent molecule (Rhodamine 110) may be used to detect the expression and/or activity of PLE, which in turn may be used to report an upstream cellular event.

5. Example

General Procedure: All non-aqueous reactions were performed in flame-dried or oven dried round-bottomed flasks under an atmosphere of argon. Stainless steel syringes or cannula were used to transfer air- and moisture-sensitive liquids. Reactions were conducted at room temperature (rt, approximately 23° C.) unless otherwise noted. Flash column chromatography was conducted using silica gel 230-400 mesh. Analytical thin-layer chromatography (TLC) was performed on E. Merck silica gel 60 F254 plates and visualized using UV, and potassium permanganate stain. Yields were reported as isolated, spectroscopically pure compounds.

Materials: Solvents were obtained from either an MBraun MB-SPS solvent system or freshly distilled. Commercial reagents were used as received Instrumentation: $^1$H NMR spectra were recorded on Bruker 400, 500, or 600 MHz spectrometers and are reported relative to deuterated solvent signals. Data for $^1$H NMR spectra are reported as follows: chemical shift ($\delta$ ppm), multiplicity (s=singlet, d=doublet, t=triplet, q=quartet, p=pentet, m=multiplet, br=broad, app=apparent), coupling constants (Hz), and integration. $^{13}$C NMR spectra were recorded on Bruker 100, 125, or 150 MHz spectrometers and are reported relative to deuterated solvent signals. LC/MS was conducted and recorded on an Agilent Technologies 6130 Quadrupole instrument.

Compound Preparation: Chemical Synthesis

N,N' bis-triflouroacetyl rhodamine (1a). To a solution of Rhodamine 110 (100 mg, 0.3 mmol) in DMF (5 mL) NaH (60%, 50 mg, 1.2 mmol) was added slowly. The mixture was allowed to stir for 1 h and triflouroacetic anhydride (170 µL, 1.2 mmol) was then added dropwise. After 16 h the reaction was quenched with AcOH (3 drops) and the mixture concentrated in vacuo. The residue was purified by flash chromatography (gradient: 4:1 hexane:EtOAc to EtOAc) to afford 122 mg (76%) of N,N'-bis-triflouroacetyl rhodamine (1a): $^1$H NMR (MeOD) $\delta$ 8.08 (d, J=7.5 Hz, 1H), 7.86 (s, J=2.1 Hz, 2H), 7.79-7.73 (m, 2), 7.38 (d, J=2.0 Hz, 2H), 7.25 (d, J=2.0 Hz, 1H), 6.86 (d, J=8.6 Hz, 2H); $^{13}$C NMR (MeOD): $\delta$108.5, 115.7, 116.3, 123.6, 124.6, 125.9, 128.2, 130.0, 135.4, 138.7, 151.2. $^{19}$F NMR (CDCl3) $\delta$−75.6; LCMS calculated for $C_{24}H_{12}F_6N_2O_5$ (M+H)$^+$ 523.1 m/z: Measured 522.9 m/z.

N,N'-bis-acetyl rhodamine (1b). To a solution of Rhodamine 110 (100 mg, 0.3 mmol) in dichloromethane (1 mL) was added acetic anhydride (60 µL, 0.6 mmol) and pyridine (100 µL, 0.57 mmol). The mixture was stirred until judged complete by TLC (1:1 hex/EtOAc). The reaction was quenched with saturated aqueous sodium bicarbonate (5 mL) and extracted with EtOAc (3×20 mL). The combined extracts were dried (MgSO$_4$), filtered and concentrated in vacuo to afford an orange solid. The residue was purified by flash chromatography (gradient: 4:1 to 1:1 hexane:EtOAc) to yield 89 mg (89%) of N,N'-bis-acetyl rhodamine (1b) as a white solid: $^1$H NMR (MeOD): $\delta$8.03 (d, J=7.6 Hz, 1H), 7.79 (s, 2H), 7.57 (m, 1H), 7.37 (d, J=6.7 Hz, 1H), 7.15 (dd, J=2.1 Hz, 2H), 6.71 (d, J=8.6 Hz, 2H), 2.14 (s, 6H). LCMS calculated for $C_{24}H_{18}N_2O_5$ (M+H)$^+$ m/z: 414.4, Measured 415.0 m/z.

N,N'-bis-propionyl rhodamine (1c). To a solution of Rhodamine 110 chloride (50 mg, 0.14 mmol) in dichloromethane (3 mL) were added propionic anhydride (40 µL, 0.30 mmol) and pyridine (50 µL, 0.286 mmol). The mixture was stirred until judged complete by TLC (1:1 hex/EtOAc). The reaction was quenched with saturated aqueous sodium carbonate (5 mL) and extracted with EtOAc (3×10 mL). The combined organic extracts were dried (MgSO$_4$), filtered and concentrated in vacuo to yield an orange solid. The residue was purified by flash chromatography with hexane/ethyl acetate (gradient: 1:1 hexane/EtOAc to EtOAc) to yield 50 mg (83%) of N,N'-bis-propionyl rhodamine (1c) as a white solid: $^1$H NMR (CDCl3): δ8.04 (d, J=7.6 Hz, 1H), 7.81-7.71 (m, 4H), 7.23-7.16 (m, 3H), 6.72 (d, J=8.8 Hz 2H), 2.42 (q, J=7.6 Hz, 4H), 1.22 (t, J=7.0 Hz, 6H). $^{13}$C NMR (MeOD): δ8.53, 29.5, 82.8, 106.9, 113.6, 115.1, 123.6, 124.4, 126.1, 127.8, 129.8, 135.2, 141.0, 151.5, 152.9, 169.8, 174.1. LCMS calculated for $C_{26}H_{22}N_2O_5$ (M+H)$^+$ m/z: 442.4, Measured 443.0 m/z.

N,N'-bis-isobutyl rhodamine (1d). To a solution of Rhodamine 110 chloride (50 mg, 0.14 mmol) in dichloromethane (3 mL) and triethylamine (100 µL, 0.682 mmol) was added isobutyryl chloride dropwise (10 µL, 0.82 mmol). The mixture was stirred until judged complete by TLC (1:1 hex/EtOAc). The reaction was concentrated in vacuo to yield a crude orange solid. The residue was purified by flash chromatography (gradient: 1:1 hexane/ethyl acetate to EtOAc) to yield 51 mg (83%) of N,N'-bis-isobutyl rhodamine (1d) as a white solid: $^1$H NMR (MeOD) δ8.03 (d, J=7.4 Hz, 1H), 7.81-7.70 (m, 4H), 7.22-7.17 (m, 3H), 6.71 (d, J=8.6 Hz, 2H), 2.65 (q, J=6.8 Hz, 2H), 1.21 (d, J=6.8 Hz, 12H); $^{13}$C NMR (MeOD) δ18.3, 35.6, 82.8, 107.1, 113.6, 115.3, 123.6, 124.4, 126.2, 127.8, 129.8, 135.3, 141.1, 151.5, 152.9, 169.8, 177.4; LCMS calculated for $C_{23}H_{18}N_2O_4$(M+H)$^+$ 470.5 m/z: Measured 471.0 m/z.

N,N'-bis-pivaloyl rhodamine (1e). To a solution of Rhodamine 110 chloride (50 mg, 0.14 mmol) in dichloromethane (2 mL) and triethylamine (100 µL, 0.682 mmol) was added trimethylacetyl chloride dropwise (40 µL, 0.30 mmol). The mixture was stirred until judged complete by TLC (1:1 hex/EtOAc). The reaction was concentrated in vacuo to yield a crude orange solid. The residue was purified by flash chromatography (gradient: 1:1 hexane/EtOAc to EtOAc) to yield 55 mg (91%) of N,N'-bis-pivaloyl rhodamine (1e) as a white solid: $^1$H NMR (MeOD): δ 8.03 (d, J=7.6 Hz, 1H), 7.79-7.69 (m, 4H), 7.26-7.19 (m, 3H), 6.71 (d, J=8.4 Hz, 2H), 1.31 (s, 18H). $^{13}$C NMR (MeOD): δ26.2, 39.3, 83.2, 108.2, 113.9, 116.3, 123.6, 124.4, 126.2, 127.6, 129.8, 135.9, 140.9, 151.4, 153.0, 170.2, 178.6. LCMS calculated for $C_{34}H_{22}N_2O_5$ (M+H)$^+$ m/z: 498.5, Measured 499.0 m/z.

N,N'-bis-benzoyl rhodamine (14 To a solution of Rhodamine 110 chloride (50 mg, 0.14 mmol) in dichloromethane (2 mL) and triethylamine (100 µL, 0.682 mmol) was added benzoyl chloride (30 µL, 0.30 mmol) dropwise. The mixture was stirred until judged complete by TLC (1:1 hex/EtOAc). When complete, the reaction was concentrated in vacuo to yield a crude orange solid. The residue was purified by flash chromatography with (gradient: 1:1 hexane/ethyl acetate to EtOAc) to yield 30 mg (42%) of N,N'-bis-benzoyl rhodamine (10 as a white solid: $^1$H NMR (CDCl3): δ8.75 (s, 2H), 8.08 (d, J=7.4 Hz, 1H), 7.92 (d, J=7.5 Hz, 1H), 7.80 (d, J=7.5 Hz, 4H), 7.66-7.55 (m, 2H), 7.47-7.41 (m, 3H), 7.33-7.30 (m, 2H), 7.25-7.21 (m, 2H), 7.12 (d, J=7.6 Hz, 1H), 6.61 (d, J=8.6 Hz, 2H). $^{13}$C NMR (CDCl3): δ83.1, 108.4, 114.0, 116.2, 124.1, 124.9, 126.0, 127.2, 128.1, 128.3, 128.5, 129.8, 130.0, 131.9, 133.5, 134.1, 135.4, 140.2, 151.4, 152.9, 166.3, 169.9. LCMS calculated for $C_{34}H_{22}N_2O_5$ (M+H)$^+$ m/z: 538.6, Measured 539.0 m/z.

Figure 2A:
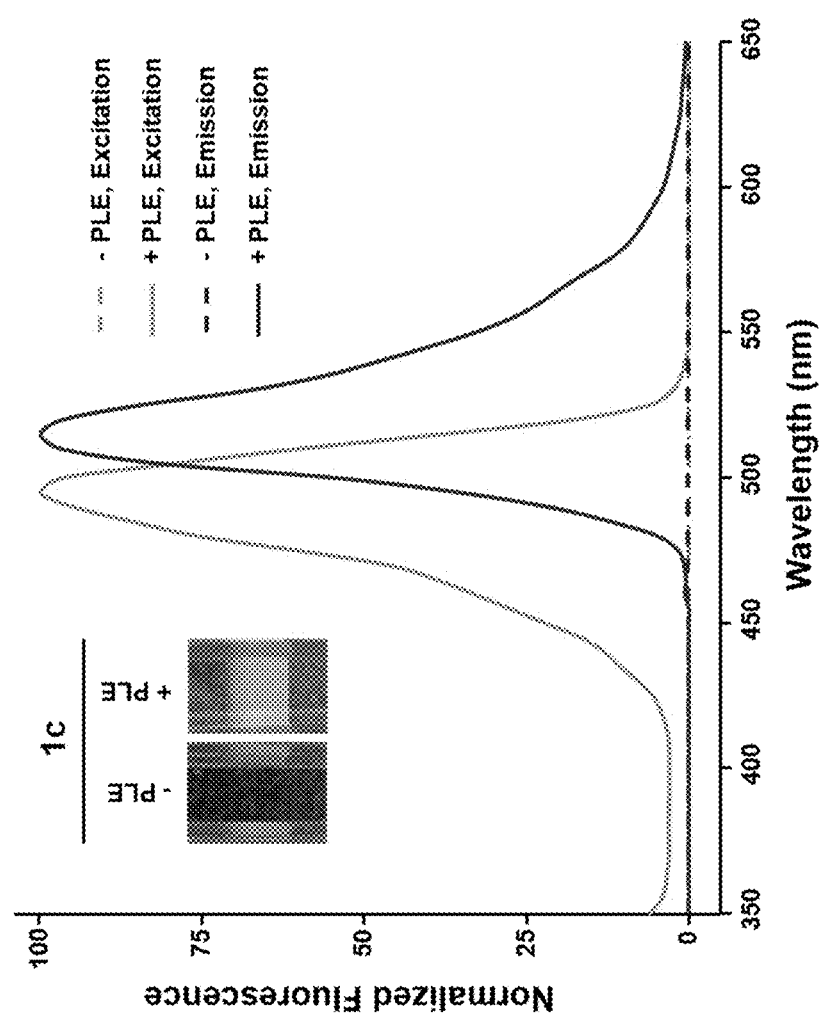
FIG. 2A and FIG. 2B show representative results from in vitro activation of amidated rhodamine pro-fluorophores by PLE.

In vitro assays. Fluorescence spectra for 1c was obtained by preparing a 10 mM solution of 1c in DMSO and diluting the solution in Hanks Balanced Salt Solution containing 10 mM HEPES-NaOH, pH 7.3 (assay buffer) to a concentration of 1 µM. Excitation (350-550 nm) and emission (450-650 nm) scans were obtained using a SpectraMax M5 (Molecular Devices). The images for the insert in FIG. 2A were acquired with an iPhone6 (Apple) while samples in cuvettes were illuminated with a hand-held, violet laser pointer.

To determine stability of rhodamine-amides in aqueous solution, 10 µM compound in assay buffer was scanned (excitation 440 nm, emission 450-650 nm) as above at time 0, 15 min, 30 min, 1 hour, 3 hours, 6 hours, 12 hours, 24 hours, and 48 hours.

Figure 5:
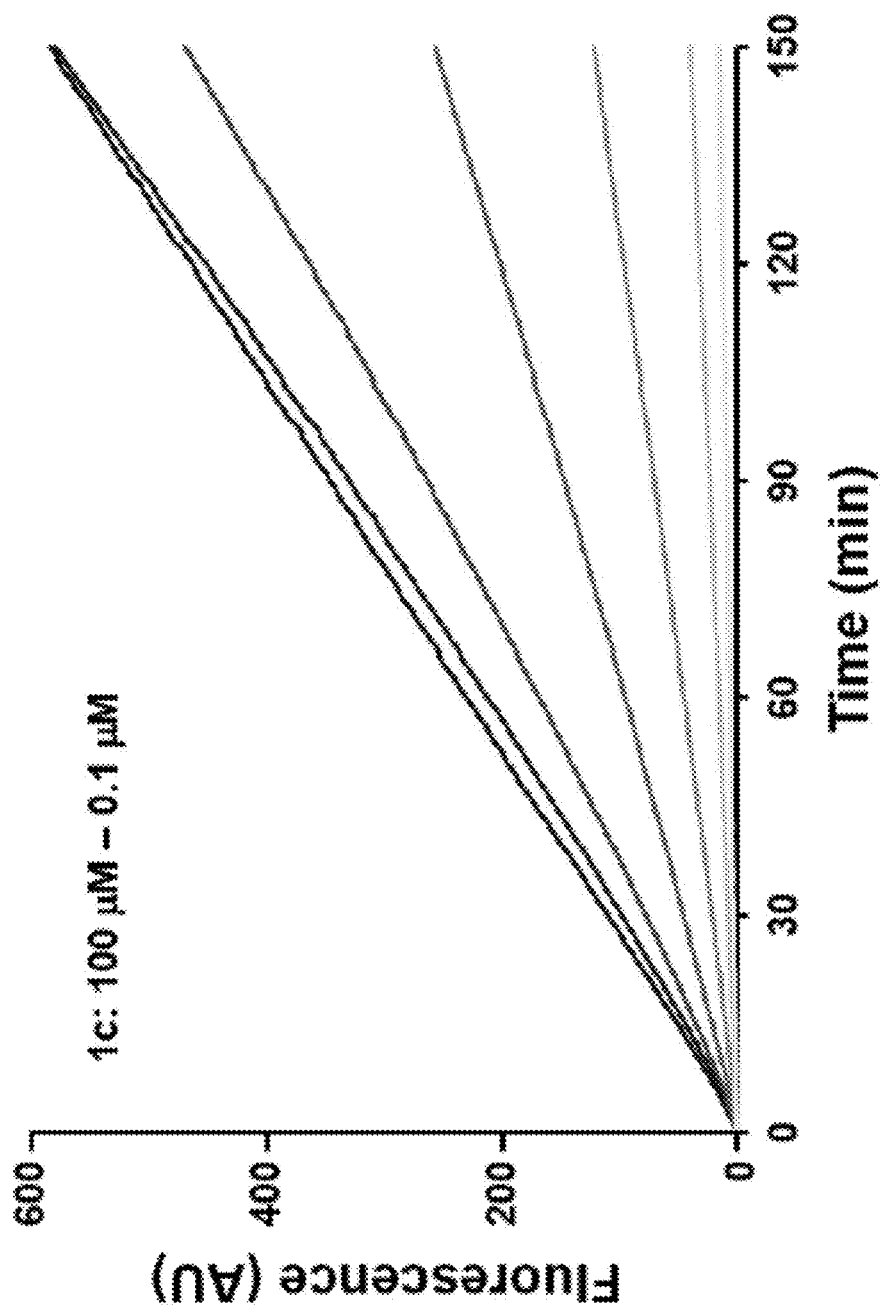
FIG. 5 shows representative results of kinetic measurements of pro-fluorophore activation by PLE. Thirty nanomolar PLE in PBS was added to a range of concentrations of compound 1c in 384-well plates and increase in fluorescence was measured with a Panoptic plate reader. The waves shown represent a concentration range of 0.1 µM-100 µM in 3-fold dilution steps. The waves shown are representative of 4 independent replicates. Data generated using this method for each of the pro-fluorophores were used to calculated kinetic parameters (Table 1).

To investigate the ability of PLE to activate various rhodamine-amide pro-fluorophores, the compounds were dissolved in DMSO to a concentration of 100 mM and serially diluted in DMSO in 10, 3-fold steps. The compounds were then added to the well of a low volume, cyclic olefin copolymer 384-well plate (Labcyte). Forty nL/well of pro-fluorophore solution were transferred to black-walled, clear-bottom, polystyrene 384-well plates (Greiner) using an Echo plate reformatter (Labcyte). Following compound transfer, 20 mL of phosphate-buffered saline (PBS) was added to each well and thoroughly mixed. PLE (Sigma, 46058) dissolved in PBS at a concentration of 60 nM and 40 µL of this solution was added to the wells of a polypropylene 384-well plate (Greiner). Pro-fluorophore-containing and PLE-containing plates were placed in a Panoptic kinetic imaging plate reader (WaveFront Biosciences). Images were acquired at 1 Hz (excitation 480±20 nm and 540±30 nm) for 30 seconds, then 20 µL/well of the PLE solutions were added to the pro-fluorophore-containing plates and imaging continued for an additional 15 minutes. In addition to the pro-fluorophore-containing plates, a plate containing PBS only was imaged as was a plate containing a concentration series of Rhodamine 110. Representative results are shown in FIG. 5 and Table 1.

TABLE 1

Kinetic parameters for PLE activation of rhodamine pro-fluorophores *

| Compound | $K_M$ (mM) | $k_{cat}/K_M$ (M$^{-1}$ S$^{-1}$) |
|---|---|---|
| 1a | 2.06 (±0.07) | 2.95 (±0.11) × 10$^4$ |
| 1b | 8.59 (±0.54) | 3.22 (±0.28) × 10$^2$ |
| 1c | 4.11 (±0.33) | 4.42 (±0.51) × 10$^3$ |
| 1d | 3.28 (±0.18) | 5.11 (±0.67) × 10$^2$ |
| 1e | 8.54 (±0.52) | 1.33 (±0.53) × 10$^3$ |
| 1f | 7.45 (±0.13) | 3.81 (±0.13) × 10$^1$ |

* Shown are $K_M$ and $k_{cat}/K_M$ values for pro-fluorophores in the presence of 30 nM PLE. Amounts of Rhodamine present at 120 seconds were calculated from a Rhodamine 110 standard curve and these values were used to determine reaction rates. $K_M$ was calculate by linear regression of reaction rates and liberated Rhodamine 110 concertation. The values represent the average of 4 independent replicates and the errors are the standard errors of the mean (SEM).

The N,N'-diacyl rhodamines were colorless, non-fluorescent (FIG. 2A), and very stable in aqueous solution in the absence of PLE ($t_{1/2}$ is approximately 2 days at 22° C. for 1a, and greater than 1 week for the other species 1b-1f), consistent with the corresponding spirocyclic structure. However, in the presence of PLE the pro-fluorophores were converted to the highly fluorescent Rhodamine 110 (FIG.

Figure 2B:
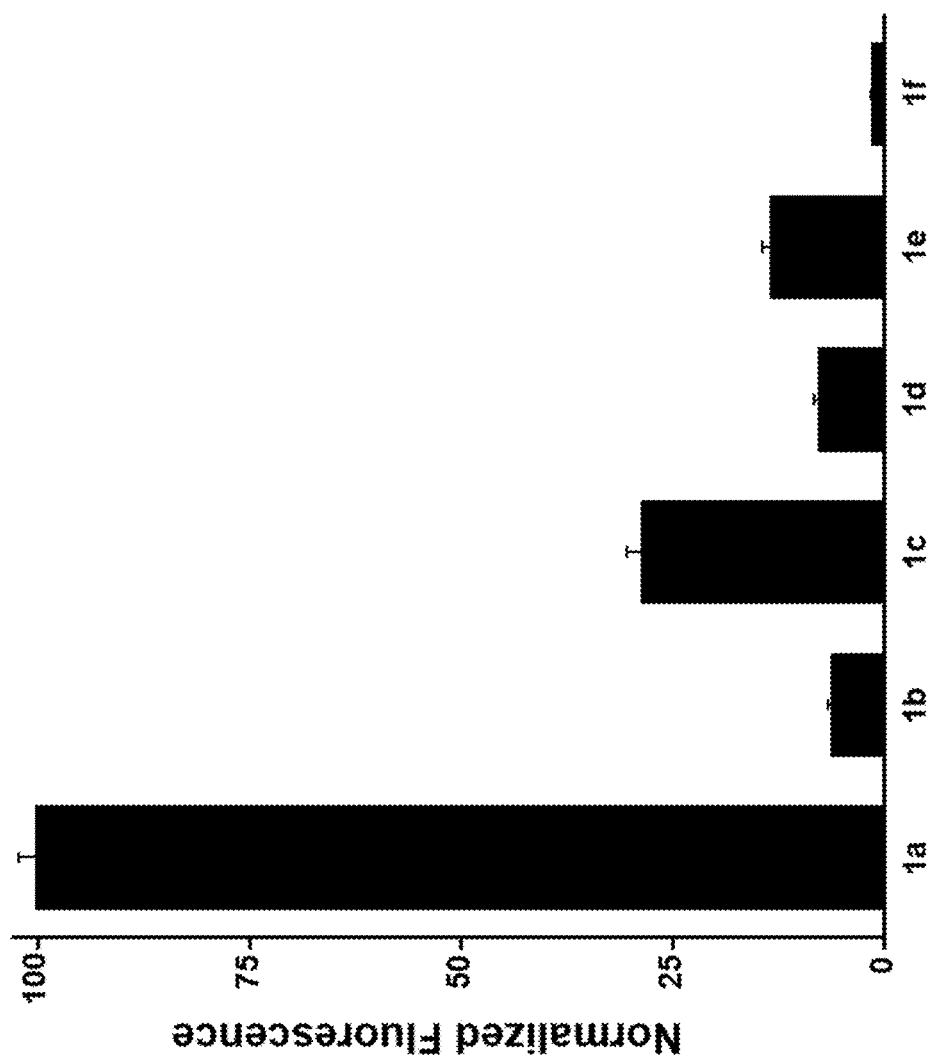

2A). Upon evaluation of the library of rhodamine-amide pro-fluorophores in vitro, it was observed that all of the pro-fluorophores were activated by PLE although some appeared to be better substrates than others with compounds 1a and 1c showing the most effective conversion to the fluorescent Rhodamine 110 under the experimental conditions herein (FIG. 2B). Calculated kinetic parameters (Table 1) ranged from a $K_M$ 2.06 µM and $k_{cat}/K_M$ 2.95×10$^4$ M$^{-1}$ S$^{-1}$ for 1a to $K_M$ 7.45 µM and $k_{cat}/K_M$ 3.81×10$^1$ M$^{-1}$ S$^{-1}$ for 1f. Without being limited by any theory, it was hypothesized that the more effective conversion of 1a by PLE may be due in part to the strongly electron-withdrawing nature of the trifluoromethyl moiety. Surprisingly, it was found, based on their steric and electronic similarity, that 1b was a less preferred substrate when compared to 1c.

Cell-based assays. To construct a PLE-expressing HEK293 cell line, a PLE-IRES-mCherry construct was excised from the pCAG-PLE-IRES-mCherry (Addgene plasmid #45766) vector using Not1-HF and Xho1 (Tian et al., *Proceedings of the National Academy of Sciences*, 2012, 109, 4756-4761). The PLE-IRES-mCherry insert was then cloned into pcDNA3.1/Zeo vector (Thermo Fisher Scientific). The pcDNA3.1/Zeo PLE-IRES-mCherry vector was introduced to HEK293 (ATCC) using FuGENE HD (Promega). PLE-expressing cells were selected for using Zeocin.

Wild-type HEK293 and PLE-expressing HEK293 cells maintained in α-MEM (Corning) containing 10% vol/vol fetal bovine serum (Thermo-Fisher Scientific) and 1% vol/vol GlutaGro (Corning) (cell culture medium) were seeded with 20,000 cells/well in 20 µL of cell culture medium into amine-coated, clear-bottom, and black-walled 384-well plate (BD Biosciences). Plates were then incubated overnight at 37° C. in a 5% $CO_2$ cell culture incubator. Following overnight incubation, cell culture medium was removed and replaced with 20 µL/well assay buffer. Rhodamine-amide profluorophores dissolved in DMSO at 10 mM were diluted into assay buffer at concentrations ranging from 50 µM-70 nM. Forty µL/well of pro-fluorophore solutions were placed in polypropylene 384-well plates (Greiner). Immediately before the beginning of data acquisition, the assay buffer was removed from the cell-containing plates. The cell-containing and pro-fluorophore containing plates where then immediately loaded into a Panoptic kinetic imaging plate reader. Images were acquired at 1 Hz (excitation 480±20 nm and 540±30 nm) for 30 seconds, then 20 µL/well of the pro-fluorophore solutions were added to the cell-containing plates and imaging continued for an additional 15 minutes. Representative results are shown in Table 2.

TABLE 2

Fold increase in fluorescence of rhodamine pro-fluorophores in HEK293 cells. *

| Compound | Fold Increase in Fluorescence |
|---|---|
| 1a | 5701 (±26.4) |
| 1b | 37 (±0.2) |
| 1c | 725 (±2.1) |
| 1d | 458 (±1.6) |
| 1e | 87 (±0.4) |
| 1f | 119 (±1.2) |

* Pro-fluorophores (10 µM) were applied to either wild-type HEK293 cells or HEK293 cells stably expressing PLE. Fold increase in fluorescence was calculated by dividing fluorescence values obtained from PLE-expressing cells by the values obtained from wild-type HEK293 cells. Fluorescence amplitudes were measured 5 min after addition of pro-fluorophores to cells. Error values represent the standard error of the mean (SEM) for 4 independent replicates.

Figure 3A:
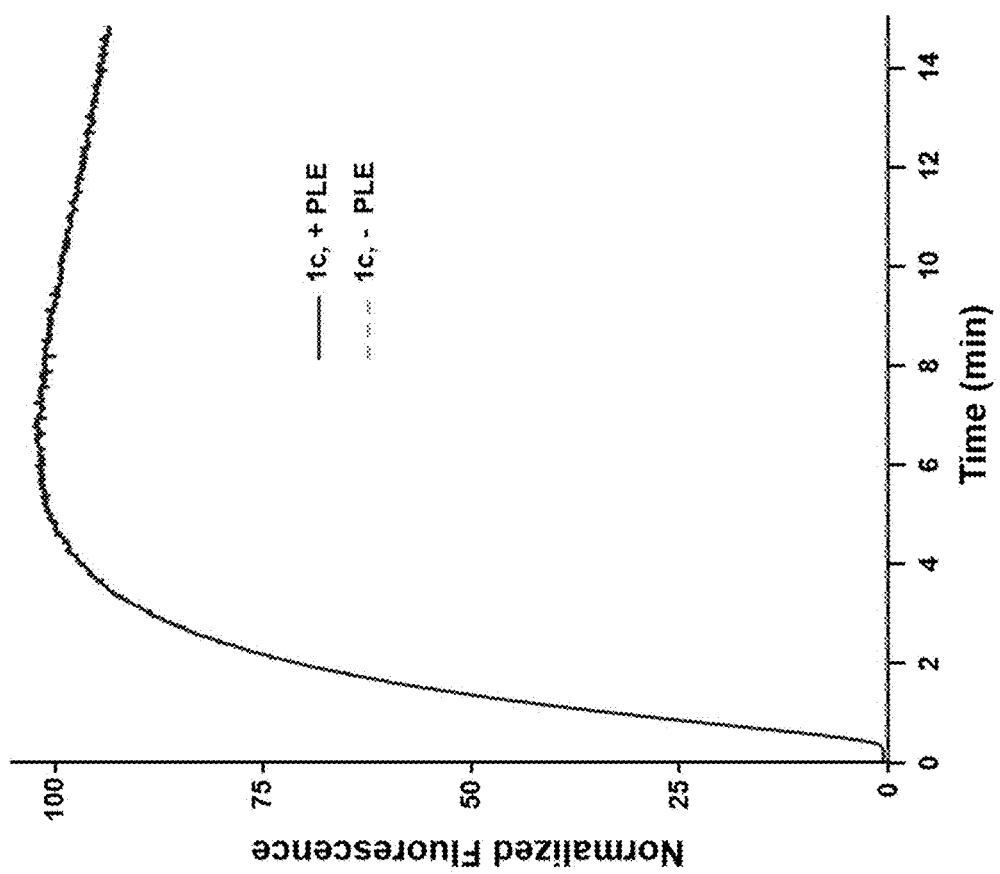
FIG. 3A and FIG. 3B show representative results from activation of amidated rhodamine pro-fluorophores in HEK293 cells.
Figure 3B:
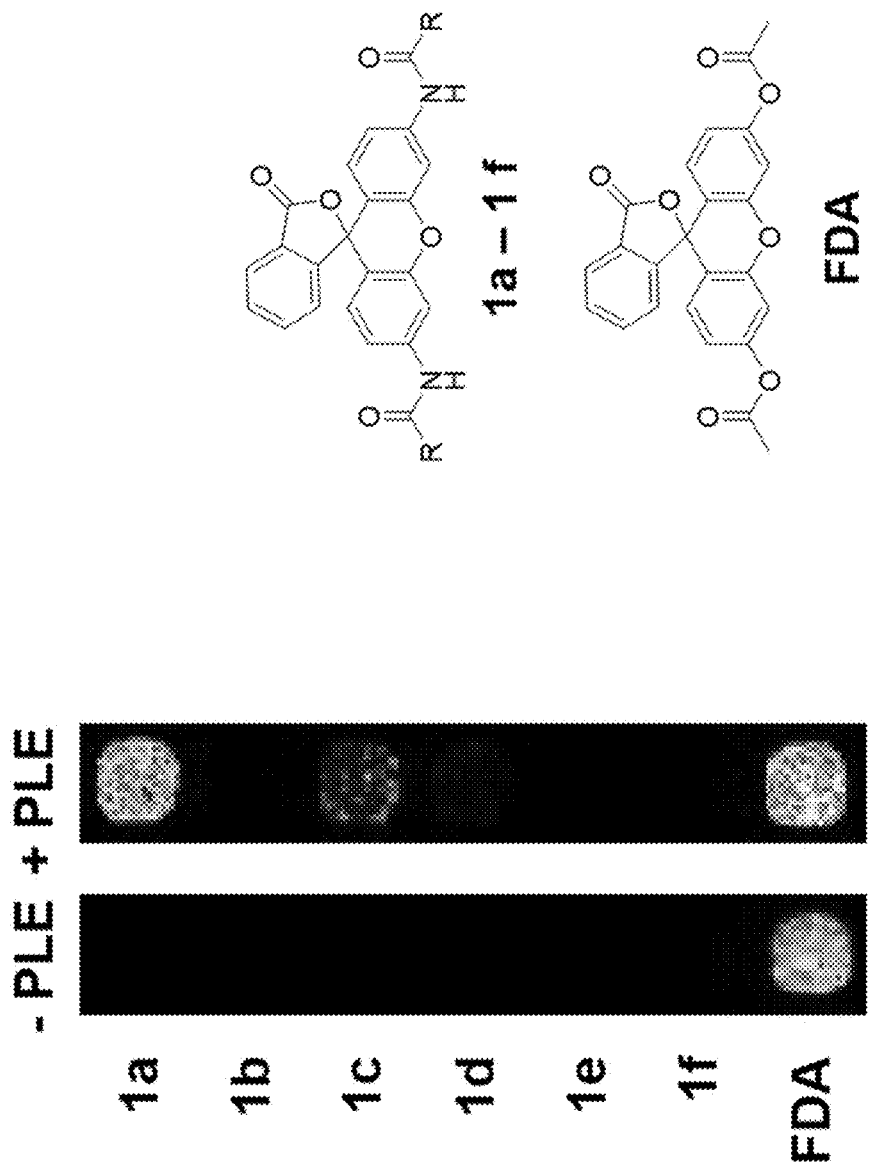

Encouraged by the in vitro results, further experiments were conducted to determine whether the acylated rhodamine pro-fluorophores disclosed herein may be used as substrates for enzymes natively expressed in a commonly used mammalian cells line, such as HEK293 cells. For these studies, a HEK293 cell line was constructed which stably expresses PLE. The acyl rhodamine pro-fluorophores were tested with both untransfected and PLE-expressing HEK293 cells. As shown in FIG. 3A, addition of 3 µM 1c to PLE-expressing HEK293 cells in a 384-well assay plate produced a rapid increase in fluorescence demonstrating that the pro-fluorophore readily enters into the cells. After the 6 min time point a modest decrease in fluorescence was noted, possibly as a result of photobleaching. However, when wild-type HEK293 cells were treated with 3 µM 1c, no increase in fluorescence was observed. FIG. 3B shows an image 384-plate wells containing ≈20000 cells per well treated with 10 µM of amidated rhodamine pro-fluorophores. In all cases where amidated rhodamine pro-fluorophores were exposed to wild-type HEK293 cells, fluorescence was not observed after 15 minutes of incubation at 22° C. However, when the rhodamine pro-fluorophores were exposed to PLE-expressing HEK cells, fluorescence was observed. The degree of fluorescence observed after 2 min for each of the samples was similar but not identical to the in vitro data with 1a and 1c producing the largest fold increase in fluorescence (Table 2). In these studies acetylated fluorescein pro-fluorophore, fluorescein diacetate (FDA), was included to demonstrate the ability of non-PLE-expressing HEK-293 cells to activate a simple ester-protected fluorescein.

As shown in FIG. 3A, fluorescence increased rapidly upon pro-fluorophore addition demonstrating the rhodamine pro-fluorophores are readily taken up into HEK293 cells. It was observed that constitutive overexpression of PLE was well tolerated by the cells with no discernable difference in growth rate or morphology compared to untransfected cells.

Although the N,N'-ditrifluoroacetyl rhodamine produced the largest increase in fluorescence, it was contemplated that further studies may suitably employ non-halogenated pro-fluorophore, such as N,N'-dipropanoyl rhodamine. Without being limited by any theory, it is hypothesized that the product of PLE's action on the rhodamine-trifluoroacetamide, such as trifluoroacetate, may be more toxic to cells than the non-halogenated products, such as propionic acid, which may be present naturally in cells and readily metabolized by the cell.

Microscopy. Confocal images were acquired using a Nikon MR (Nikon Instruments) laser scanning confocal microscope equipped with plan apochromat violet corrected 1.4 numerical aperture (N.A.) oil immersion lens. Hoescht images were obtained using a 405 nm laser and 425-475 nm emission filter. Pro-fluorophore (1c) was imaged using a 488 nm laser and 500-550 nm emission filter. Cells for imaging study were cultured overnight on no. 1 chambered slides (lab-tek II, ThermoFisher) in medium previously described in kinetic imaging assays. Medium was removed and pro-fluorophore was added to the slide chambers in assay buffer containing Hoescht, 1 µg/mL. The slides were imaged after a 5 min incubation at room temperature.

Figure 4:
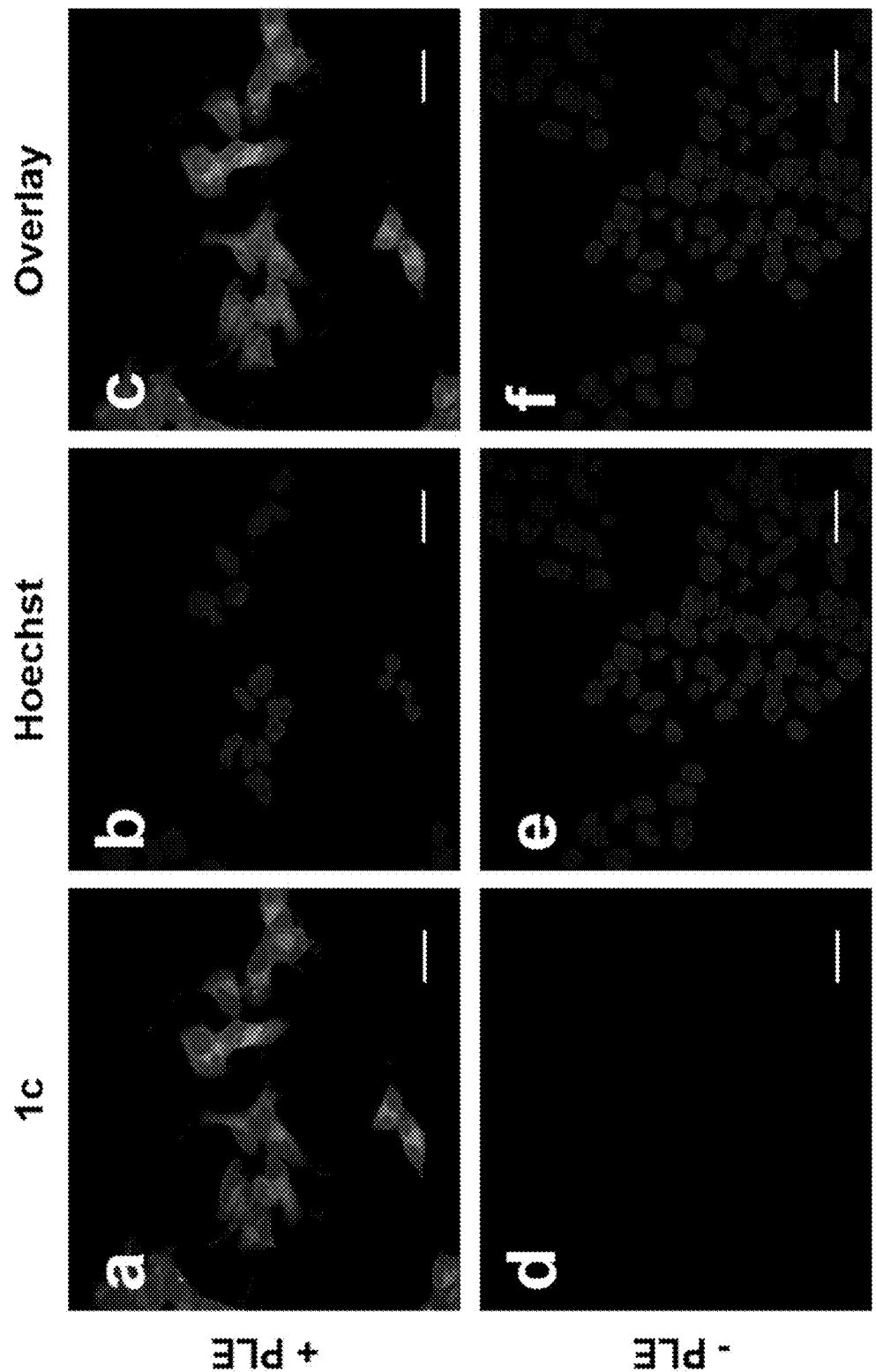
FIG. 4 shows representative results from confocal imaging of HEK293 cells treated with amidated rhodamine pro-fluorophore, 1c. Panels a-c show images of a set of PLE-expressing HEK293 cells treated with 1c and the DNA-specific fluorescent dye, Hoechst. Panels d-f show images of a set of wild-type HEK293 cells treated under the same conditions as panels a-c. The scale bar shown in the lower right of each image is 20 µm. Images are representative of 4 independent replicates.

Based on the observation that 1c was rapidly activated in HEK293 cells, the suitability of the 1c for cellular imaging was determined. Confocal fluorescence microscopy was used to visualize HEK293 cells treated with 1c for 1 h at 22° C. As shown in FIG. 4 (panels d-f), no fluorescence was observed in wild-type cells. However, HEK293 cells expressing PLE showed bright, predominantly cytoplasmic, fluorescence (FIG. 4, panels a-c). These data clearly demonstrate the utility of the rhodamine-propanamide pro-fluorophore/PLE enzyme pair for cellular imaging of PLE-expressing cells.

In summary, per-acylation of commercial Rhodamine 110 was carried out to provide rhodamine pro-fluorophores, which were released upon exposure to PLE in vitro and in cells. It was demonstrated that these pro-fluorophores were very stable in aqueous solution and in wild-type HEK293 cells but that they could be converted to the fluorescent Rhodamine 110 by PLE in vitro as well as in HEK293 cells engineered to express PLE. Under the conditions described herein, the N,N'-ditrifluoroacetyl and N,N'-dipropionyl rhodamine pro-fluorophores were better substrates than the others disclosed herein. Further, it was found that N,N'-dipropionyl rhodamine pro-fluorophore showed bright, cytoplasmic fluorescence in PLE-expressing cells thus demonstrating suitability for cellular imaging.

Recent reports demonstrated the utility of PLE for activating rhodamine-based pro-fluorophores using the trimethyl lock approach and re-evaluated prior work with rhodamines released by serine hydrolase with varying peptide pro-fluorophore scaffolds. Although compound 1b was previously prepared (Lavis et al., ACS Chemical Biology 2006, 1, 252-260), testing of 1b as a substrate for PLE was not reported. Remarkably, although 1b appears to be a poor substrate for PLE, the closely related and equally easy to prepare 1a and 1c are good PLE substrates suitable for in vitro and cell-based use. It is important to note that in the previous studies the action of PLE on an ester indirectly results in the liberation of the Rhodamine 110 in contrast to the direct, amidase mechanism observed here with the pro-fluorophores in the present disclosure. Thus, the present disclosure extends the use of PLE as a pro-fluorophore activating enzyme for Rhodamine 110 via a different mechanism which takes advantage of PLE's amidase activity to catalyze the release of Rhodamine 110 from simple rhodamine amide pro-fluorophores.

It is contemplated that cell-type specific expression of PLE may enable discrimination of PLE-expressing cells from non-expressing cells in cell culture as well as in tissues and whole organisms. While the experiments herein did not observe any measurable level of conversion of the pro-fluorophores to Rhodamine 110 in wild-type HEK293 cells, it should be noted that other cell types may contain natively expressed enzyme activities which may interfere with the use of the pro-fluorophores.

The foregoing discussion discloses and describes merely exemplary embodiments of the invention. One skilled in the art will readily recognize from such discussion and from the accompanying drawings and claims, that various changes, modifications and variations can be made therein without departing from the spirit and scope of the invention as defined in the following claims.

We claim:

1. A method comprising reacting a compound of formula (I), or salt thereof, with a porcine liver esterase (PLE),

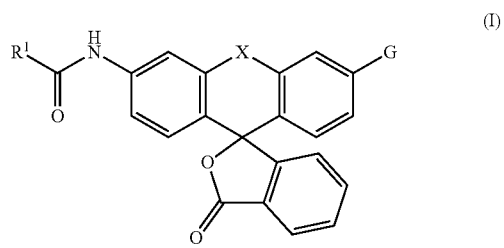

wherein
X is O, $CR^xR^y$, or $SiR^xR^y$;
G is —OH, —$NH_2$, —OC(O)$R^2$, or —NHC(O)$R^2$;
$R^x$ and $R^y$ are each independently H or $C_{1-4}$alkyl;
$R^1$ and $R^2$ are independently $C_{1-6}$alkyl, $C_{1-6}$haloalkyl, $C_{3-8}$cycloalkyl, 6- to 10-membered aryl, 5- to 8-membered heteroaryl, or 5- to 8-membered heterocycle, wherein the cycloalkyl, aryl, heteroaryl, and heterocycle are optionally substituted, wherein the heteroaryl and heterocycle are attached to the —C(O)— group through a carbon atom; and
wherein the porcine liver esterase directly catalyzes a hydrolysis of the —C(O)—NH— groups of the compound of formula (I), or salt thereof,
whereby a fluorescence signal is produced.

2. The method of claim 1, further comprising contacting the compound, or salt thereof, with a sample comprising the porcine liver esterase.

3. The method of claim 2, wherein the sample is a cell.

4. The method of claim 3, wherein the compound, or salt thereof, enters the cell.

5. The method of claim 3, wherein the cell expresses the porcine liver esterase.

6. The method of claim 5, wherein the expression does not cause discernable difference in growth rate or morphology of the cell.

7. The method of claim 1, further comprising measuring the fluorescence signal.

8. The method of claim 2, further comprising imaging the sample.

9. The method of claim 8, wherein the imaging comprises visualizing the sample by fluorescence microscopy.

10. The method of claim 1, wherein the compound is a compound of formula (I-a), or a salt thereof,

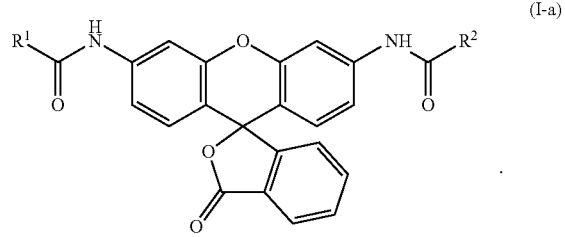

11. The method of claim 10, wherein $R^1$ and $R^2$ are independently $C_{1-6}$alkyl, $C_{1-6}$haloalkyl, or phenyl.

12. The method of claim 10, wherein $R^1$ and $R^2$ are independently $C_{1-4}$alkyl or —$CF_3$.

13. The method of claim 10, wherein $R^1$ and $R^2$ are both —$CH_2CH_3$, i-$C_3H_7$, or —$CF_3$.

14. The method of claim 10, wherein $R^1$ and $R^2$ are both —$CH_2CH_3$.

\* \* \* \* \*